United States Patent
Shivpure et al.

(10) Patent No.: US 12,186,110 B2
(45) Date of Patent: Jan. 7, 2025

(54) NON-INVASIVE NON-CONTACT SYSTEM AND METHOD FOR EVALUATING PRIMARY AND SECONDARY HYPERTENSION CONDITIONS USING THERMAL IMAGING

(71) Applicant: Aarca Research Inc., Orange, CT (US)

(72) Inventors: Sameer Raghuram Shivpure, Maharashtra (IN); Jayanthi Thiruvengadam, Tamil Nadu (IN); Anuhya Choda, Andhra Pradesh (IN); Gayathri Choda, Andhra Pradesh (IN)

(73) Assignee: AARCA RESEARCH INC., Orange, CT (US)

(*) Notice: Subject to any disclaimer, the term of this patent is extended or adjusted under 35 U.S.C. 154(b) by 277 days.

(21) Appl. No.: 17/291,682

(22) PCT Filed: Oct. 11, 2020

(86) PCT No.: PCT/IB2020/059537
§ 371 (c)(1),
(2) Date: May 6, 2021

(87) PCT Pub. No.: WO2021/084352
PCT Pub. Date: May 6, 2021

(65) Prior Publication Data
US 2022/0280121 A1 Sep. 8, 2022

(30) Foreign Application Priority Data
Oct. 31, 2019 (IN) ............................. 201941044161

(51) Int. Cl.
*A61B 5/00* (2006.01)
*A61B 5/01* (2006.01)
(Continued)

(52) U.S. Cl.
CPC ............ *A61B 5/7275* (2013.01); *A61B 5/015* (2013.01); *A61B 5/02141* (2013.01);
(Continued)

(58) Field of Classification Search
None
See application file for complete search history.

(56) References Cited

U.S. PATENT DOCUMENTS 5,991,653 A * 11/1999 Richards-Kortum ........................ A61B 5/0084
436/171
7,435,221 B1 * 10/2008 Bharmi .................... A61B 5/08
600/509
(Continued)

FOREIGN PATENT DOCUMENTS

| WO | 2019061418 A1 | 4/2019 | |
| WO | WO-2019116996 A1 * | 6/2019 | ........... A61B 5/0022 |
| WO | 2019180065 A1 | 9/2019 | |

OTHER PUBLICATIONS

English machine translation of WO 2019116996 A1, Clarivate Analytics, 15 pages, printed on Mar. 30, 2024 (Year: 2024).*
(Continued)

*Primary Examiner* — Matthew Kremer
(74) *Attorney, Agent, or Firm* — Morse, Barnes-Brown & Pendleton, P.C.; Martin Z. Zhang, Esq.

(57) ABSTRACT

System and method for measuring hypertension conditions of a subject is disclosed. The disclosed system and method includes thermal sensors for capturing thermal images and/or videos of a body part; and a processing engine to detect a predefined region of the body part in each frame of the captured images and/or videos. The processing engine segments one or more portions from the detected predefined region in each frame of the captured images and/or videos to identify a region of interest comprising arteries in the one or
(Continued)

more segmented portions. Based on the identified region of interest, the engine extracts pixel values from each frame of the captured images and/or videos to determine parameters associated with a blood flow velocity and a blood pressure of the subject. Further a type of hypertension and a risk score for the hypertension condition based on the determined parameters using computational models are measured.

17 Claims, 6 Drawing Sheets

(51) Int. Cl.
    *A61B 5/021*      (2006.01)
    *A61B 5/026*      (2006.01)
    *G06T 7/00*       (2017.01)
    *G06T 7/174*      (2017.01)
    *A61B 5/02*       (2006.01)

(52) U.S. Cl.
    CPC .......... *A61B 5/0261* (2013.01); *A61B 5/7264* (2013.01); *G06T 7/0012* (2013.01); *G06T 7/174* (2017.01); *A61B 5/02007* (2013.01); *G06T 2207/30104* (2013.01)

(56) References Cited

U.S. PATENT DOCUMENTS

| | | | |
|---|---|---|---|
| 2004/0254472 A1* | 12/2004 | McQuilkin | A61B 5/015 600/549 |
| 2009/0281423 A1* | 11/2009 | Sirohey | A61B 6/504 600/431 |
| 2016/0007865 A1 | 1/2016 | Sakata et al. | |
| 2016/0073908 A1* | 3/2016 | Khachaturian | G01K 7/42 600/474 |
| 2016/0360980 A1* | 12/2016 | Sinha | A61B 5/02427 |
| 2017/0079533 A1* | 3/2017 | Robinson | A61B 5/02116 |
| 2017/0245768 A1 | 8/2017 | White et al. | |
| 2018/0088051 A1* | 3/2018 | Georgakoudi | G06T 7/20 |
| 2020/0214647 A1* | 7/2020 | Peng | A61B 5/02 |

OTHER PUBLICATIONS

Primary Hypertension (Formerly Known as Essential Hypertension), Cleveland Clinic, my.clevelandclinic.org/health/diseases/22024-primary-hypertension-formerly-known-as-essential-hypertension, 11 pages, printed on Aug. 2, 2024 (Year: 2024).*
Secondary Hypertension, Cleveland Clinic, my.clevelandclinic.org/health/diseases/21128-secondary-hypertension, 10 pages, printed on Aug. 2, 2024 (Year: 2024).*
International Search Report for International Application No. PCT/IB2020/059537 mailed Jan. 26, 2021.

* cited by examiner

NON-INVASIVE NON-CONTACT SYSTEM AND METHOD FOR EVALUATING PRIMARY AND SECONDARY HYPERTENSION CONDITIONS USING THERMAL IMAGING

CROSS REFERENCE TO RELATED APPLICATIONS

This application claims priority to International Patent Application No. PCT/IB2020/059537, filed on Oct. 11, 2020, which claims priority to Indian patent application No. 201941044161, filed on Oct. 31, 2019. The contents of these applications are hereby incorporated by reference in their entirety.

TECHNICAL FIELD

The present disclosure generally relates to the technical field of health care systems for evaluating health condition of a person. More particularly, the present disclosure relates to a non-contact, non-invasive system and method for evaluating primary and secondary hypertension conditions of a person using thermal imaging.

BACKGROUND

The background description includes information that may be useful in understanding the present invention. It is not an admission that any of the information provided herein is prior art or relevant to the presently claimed invention, or that any publication explicitly or implicitly referenced is prior art.

Hypertension is a chronic medical condition in which a blood pressure in arteries is persistently elevated. Blood pressure is a force exerted by circulating blood against arterial walls of an individual, and it may depend on resistance from the arterial walls or whole blood viscosity. An excessive blood pressure than normal exerted because of increased peripheral resistance is determined as the hypertensive conditions. Excessive pressure can harden the arteries, thus impacting an amount of blood flow to a heart and brain of the individual. Hypertension, if diagnosed, can be controlled but still may cause complications that could be life-threatening. Persistently elevated blood pressure significantly increases the risk of cardiovascular, cerebrovascular, renal and other fatal diseases. Hypertension may not have symptoms and hence, can be undetected for a long time until medically diagnosed. When symptoms do occur, it includes morning headaches, lightheadedness, vision changes, buzzing in ears and irregular heart rhythms. Severe hypertension can cause fatigue, nausea, vomiting, confusion, anxiety, chest pain, and muscle tremors. The risk of high blood pressure increases with age and may never be diagnosed until the blood pressure has reached a severe or life-threatening stage.

Hypertension results from a combination of causes and contributing factors, including an individual's lifestyle and genetics. Hypertension is mainly classified as a primary (essential) hypertension and a secondary hypertension. The primary hypertension is a most prominent type and can be associated with genetic factors, blood plasma volume or nonspecific lifestyle. The secondary hypertension is associated with specific identifiable underlying causes, such as chronic kidney disease, diabetes, obesity, hyperthyroidism, long-term hypothyroidism or other endocrine disorders. The factors that increase the risk of hypertension include age, ethnicity, family history, tobacco usage, alcohol consumption and stress. Lifestyle factors can include dietary habits, level of physical activity, long term usage of medication and others.

Diagnosis, continuous monitoring and treatment are essential in managing the primary and secondary hypertension conditions. Complications associated with hypertension, such as nephropathy, neuropathy, cardiovascular and cerebrovascular diseases can be prevented or delayed with continuous monitoring and appropriate treatment plan. Clinical diagnosis of the hypertension typically involves measuring systolic and diastolic blood pressures. The systolic pressure represents pressure in the arteries when the heart contracts or beats. The diastolic pressure represents pressure in the arteries when the heart rests between beats. Persistently elevated blood pressure over time, confirms hypertension condition in a person. For a normal adult, the systolic pressure is in the range of 110-130 mmHg and the diastolic pressure is in the range of 70-90 mmHg. Hypertension is diagnosed if, when the blood pressure repeatedly measured over a period of time, the systolic blood pressure is persistently ≥130 mmHg and/or diastolic blood pressure is persistently ≥90 mmHg.

In patients having elevated blood pressure, it is important to further evaluate the symptoms and other health conditions to diagnose hypertension as the primary condition or secondary condition. Among the hypertensive population, since primary hypertension is prevalent and the secondary forms are rare, the patients are subjected to limited evaluation due to time-consuming and expensive laboratory tests to identify the underlying disorders. The secondary hypertension if not properly diagnosed can cause resistant hypertension and can increase the complications associated with the underlying cause.

The blood pressure measurement currently comprises techniques such as Auscultation, Cuff Oscillometry, Ultrasound Sphygmomanometer measurement and Ambulatory monitoring. These methods are non-invasive but require placing a cuff typically around the upper arm to measure the pressure in the brachial artery. These methods/techniques are sensitive to physical movements and require the subject/patient to be relaxed and to maintain proper body posture, causing discomfort or white coat effect in measurement. Moreover, the cuff used for the measurement may not be of appropriate size relative to the arms or the devices used to measure the blood pressure may not be accurate always, leading to inaccurate or inconsistent readings. It may be difficult to obtain reproducible results. Further, additional diagnostic tests such as blood tests, ECG and scans are required to check for the possibility of secondary hypertension which are expensive. Hence, these methods may require careful observation by a physician and may not be suitable for continuous monitoring or multiple pre-screenings.

Among hypertension patients, a few home-based electronic blood pressure monitors are preferred to monitor the blood pressure levels regularly. However, electronic blood pressure monitors may not be accurate and need to be validated according to standard international testing protocols. Also, the measurement requires placing the cuff firmly and adequately over the upper arm for accurate blood pressure readings, which may result in poor adherence to self-monitoring. The prior techniques that used infrared emission measurements are not explicitly equipped for risk stratification of the hypertensive patients who present without symptoms of increased blood pressure. These prior techniques fail to combine new thermal detectors with a clinical procedure for stimulating homeostasis and measuring the related vascular function. A significant reason is that no simple and unambiguous laboratory test has existed that can be used to identify those subjects who are at risk of developing hypertension or prehypertension or identifying secondary hypertension.

There is, therefore, a need to provide a simple and efficient solution to identify subjects with either pre-hypertension or hypertension conditions so that they can take precautions or obtain treatment early, and can also monitor progression of the disease over time.

OBJECTS OF THE INVENTION

A general object of the present disclosure is to provide a simple and efficient solution which can obviate the foregoing limitations in the art.

An object of the present disclosure is to provide an improved system for evaluating hypertension conditions of an individual.

Another object of the present disclosure is to provide an efficient system to identify individuals' risk for pre-hypertension or hypertension and to determine between primary and secondary forms so that they can obtain treatment early, and can also monitor progression of the disease over time.

Another object of the present disclosure is to provide a non-contact, non-invasive system and method for evaluating a primary hypertension condition and/or a secondary hypertension condition of a person by measuring vascular health using thermal imaging.

Yet another object of the present disclosure is to provide an efficient system and method to use biomarkers associated with vascular health and various hemodynamic factors determined from thermal imaging for measuring hypertension conditions of individuals to help in diagnosis of the health conditions.

Still another object of the present disclosure is to provide a simple and cost-effective system and method which can be easily implemented for evaluating both primary and secondary hypertension conditions of a person.

SUMMARY

Aspects of the present disclosure relate to a non-contact, non-invasive system and method for evaluating primary and secondary hypertension conditions in a person. The proposed system and method may be used for pre-diagnosis of hypertension or for deciding between primary and secondary forms or for regulating medications or treatment suitable to the patient over time. This system and method may also be used for the early detection of biomarkers indicating risk of developing the hypertension condition, and can use biomarkers associated with elevated blood pressure or increased whole blood viscosity measured by thermal imaging for assessing the complications associated with hypertension.

The elevated blood pressure or an increase in whole blood viscosity of a person may cause coronary artery disease over time, such as arteriosclerosis. These complications modify the vascular structure and cause hemodynamic imbalances in the body. These imbalances can be seen in carotid arteries and are used as potential biomarkers to determine hypertension conditions. The blood flow through the arteries emits heat due to peripheral resistance of arterial walls and is measured using sensitive thermal sensors. The elevated blood pressure in the carotid arteries exerts more pressure on the arterial walls and changes the hemodynamics. The elevated pressure exerted on the wall causes temperature variation in the arterial region and is used as a principle behind this method to measure parameters associated with hemodynamics. Further, the parameters measured are evaluated to identify differences corresponding to the primary and secondary form of hypertensions. These differences serve as biomarkers of the primary and secondary hypertension conditions.

In an aspect, the disclosed system and method for determining hypertension condition of a subject, such as a human, are based on capturing any or a combination of one or more thermal images and videos of at least one body part, for example an anterior face, of the subject by a set of thermal sensor; and receiving a set of data packets associated with the captured any or a combination of one or more images and videos by a processing engine. The processing engine comprises processors coupled to a memory storing a set of instructions executable by the one or more processors to detect a predefined region, for example a face, of the body part in each frame of the captured images and/or videos, and segment one or more portions, a forehead, from the detected predefined region in each frame of the captured images and/or videos. A region of interest comprising arteries in the segmented portions in each frame of the captured images and/or videos is automatically identified, and further the identified region of interest from each of the captured images and/or videos is segmented by the processors.

In an embodiment, one or more pixel values, representing a set of bio signals, from each frame of the captured images and/or videos is extracted based on the segmented region of interest by the processors so as to determine one or more parameters associated with a blood flow velocity and a blood pressure of the subject based on the extracted one or more pixel values. The determined one or more parameters are compared with predetermined set of reference parameters to measure a risk score for the hypertension condition of the subject based on the comparison using computational models. A primary hypertension condition and a secondary hypertension condition are determined based on the measured risk score for the hypertension condition. Thus, it would be appreciated that the risk score for the hypertension condition is determined non-invasively without contacting the subject and does not involve any harmful radiation.

In an embodiment, the determined one or more parameters associated with the blood flow velocity and the blood pressure correspond to the time and frequency domain parameters including, but not limited to, average intensity, signal amplitude, signal period, signal entropy, signal power spectral density, histogram and peak count.

In an exemplary embodiment, the disclosed system and method can be used for various applications, for example a pre-diagnosis of the hypertension condition, to identify between the primary and secondary form of hypertensions, regulate medications and treatment suitable to a hypertension patient over time, early detection of biomarkers indicating the risk of developing the hypertension condition, determine efficacy of lifestyle and medical interventions.

Various objects, features, aspects and advantages of the inventive subject matter will become apparent from the following detailed description of preferred embodiments, along with the accompanying drawing figures in which like numerals represent like components.

BRIEF DESCRIPTION OF THE DRAWINGS

In the figures, similar components and/or features may have the same reference label. Further, various components of the same type may be distinguished by following the reference label with a second label that distinguishes among the similar components. If only the first reference label is used in the specification, the description is applicable to any one of the similar components having the same first reference label irrespective of the second reference label.

DETAILED DESCRIPTION

The following is a detailed description of embodiments of the disclosure depicted in the accompanying drawings. The embodiments are in such detail as to communicate the disclosure. However, the amount of detail offered is not intended to limit the anticipated variations of embodiments; on the contrary, the intention is to cover all modifications, equivalents, and alternatives falling within the spirit and scope of the present disclosure as defined by the appended claims.

If the specification states a component or feature "may", "can", "could", or "might" be included or have a characteristic, that particular component or feature is not required to be included or have the characteristic. As used in the description herein and throughout the claims that follow, the meaning of "a," "an," and "the" include plural reference unless the context clearly dictates otherwise. Also, as used in the description herein, the meaning of "in" includes "in" and "on" unless the context clearly dictates otherwise.

Various methods described herein may be practiced by combining one or more machine-readable storage media containing the code according to the present invention with appropriate standard computer hardware to execute the code contained therein. An apparatus for practicing various embodiments of the present invention may involve one or more computers (or one or more processors within the single computer) and storage systems containing or having network access to a computer program(s) coded in accordance with various methods described herein, and the method steps of the invention could be accomplished by modules, routines, subroutines, or subparts of a computer program product.

While embodiments of the present invention have been illustrated and described, it is apparent that the invention is not limited to these embodiments only. Numerous modifications, changes, variations, substitutions, and equivalents will be apparent to those skilled in the art, without departing from the spirit and scope of the invention, as described in the claim.

Embodiments explained herein relate to health care systems for evaluating health condition of an individual/patient. In particular, the present disclosure relates to a non-contact, non-invasive system and method for evaluating primary and secondary hypertension conditions of a person using thermal imaging.

In an aspect, the present disclosure provides a system and method for measuring hypertension conditions of a person. The system and method includes a set of thermal sensors for capturing one or more thermal images or a thermal video of at least one part of a subject body; and a processing engine operatively coupled to the set of thermal sensors, the processing engine comprising a processor coupled to a memory, the memory storing instructions executed by the processor to: pre-process the received one or more thermal images/videos; for each image/video from the set of thermal images captured or from the captured thermal videos, define a region of interest (ROI) in each of the image frames; segment the ROI in each of the plurality of image frames into a plurality of segments based on thermal gradient pattern; determine a change in thermal gradient values of each pixel in the ROI for a predefined time period to obtain set of time domain values for quantitative analysis and signal processing; determine one or more parameters associated to a blood flow velocity and a blood pressure of the subject; and compare the determined parameters with a set of predetermined or predefined parameters values observed for healthy subjects to determine inconsistencies associated to the hypertension condition.

In another aspect, the system and method for measuring primary and secondary conditions uses passive thermal videos/images of an anterior face of a subject to measure vascular function and analyze the blood transmission pattern. The frontal branches of major arteries on the forehead, is considered to measure biomarkers of vascular dysfunction. The frontal branches of the carotid arteries typically lay close to a skin surface in the forehead region, and the heat intensity can be measured from the thermal video captured using an infrared thermal camera. The region related to the arterial structure in the forehead is automatically segmented from each frame of the videos/images. The segmented region is further processed to extract the pixel values representing distribution of temperature or the heat intensity along the arterial section. Time domain values are evaluated using statistical analysis and signal processing techniques to calculate parameters associated with a blood flow velocity and a blood pressure of the subject.

These parameters represent hemodynamics such as, but not limited to, blood flow velocity, pulse rate, blood density and blood pressure. The variations in the thermal intensity along the segmented region represent the blood flow through the vascular region. By relating the variations in the intensity of heat and the measured parameters with age of the subject and by comparison with corresponding measurements initially determined from normotensive subjects of comparable age, the presence of hypertension is determined. Moreover, imbalances in the hemodynamic parameters in the ROI are observed in hypertensive patients. These factors and their magnitude are considered to measure the severity of the hypertension condition of the subject.

In an embodiment, the disclosed system and methods can be used to identify efficacy of the therapeutic intervention, such as to manage dosage overtime of anti-hypertensive medication, or to assess success of lifestyle interventions or other treatments to modify disease progression.

Figure 1:
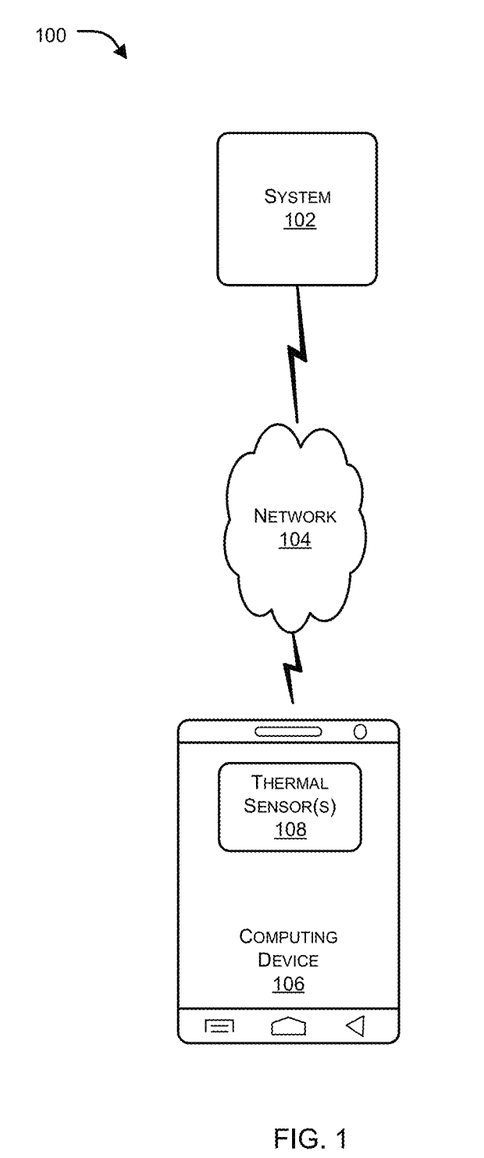
FIG. 1 illustrates an exemplary overall architecture in which or with which the proposed system can be implemented, in accordance with an embodiment of the present disclosure.

FIG. 1 illustrates an exemplary overall architecture in which or with which the proposed system can be implemented, in accordance with an embodiment of the present disclosure.

In an embodiment, an overall architecture 100 includes a system 102 that can be implemented in any computing device that can be configured/operatively coupled with a server. The system 102 can be implemented using any or a combination of hardware components and/or software components such as a server, a computing system, a computing device, a security device and the like, such that embodiments of the present disclosure can determine the hypertension condition for a person. The system 102 can include processors and a memory storing instructions executable by the processors. Further, the system 102 can be communicatively coupled with a computing device 106 through a network 104. The computing device 106 can be integrated with a set of thermal sensors 108. The set of thermal sensors 108 can be any or a combination of, but not limited to, a digital camera, a digital single-lens reflex (DSLR) camera, a standalone infrared camera, a thermal camera, or a monochromatic camera. Those skilled in the art would appreciate that the thermal image can be captured using a thermal camera, the thermal camera senses thermal or infrared radiation emitted from the body of the person and can render images representing the spatial intensity of radiation. Since the images can be captured from an optimal distance, therefore this technique is non-invasive and non-contact.

The network 104 can be a wireless network, a wired network or a combination thereof that can be implemented as one of the different types of networks, such as Intranet, Local Area Network (LAN), Wide Area Network (WAN), Internet, and the like. Further, the network 104 can either be a dedicated network or a shared network. The shared network can represent an association of the different types of networks that can use a variety of protocols, for example, Hypertext Transfer Protocol (HTTP), Transmission Control Protocol/Internet Protocol (TCP/IP), Wireless Application Protocol (WAP), and the like.

Examples of the computing devices 106 can include, but are not limited to, a portable computer, a personal digital assistant, a handheld device, and a workstation. In an embodiment, the computing device 106 is a mobile phone having the imaging device 108. In another embodiment, the imaging device 108 is operatively coupled with the computing device 106. In an embodiment, system 102 facilitates a non-invasive and non-contact technique for determining biomarkers to help determine the hypertension condition of the person.

In an embodiment, the thermal sensor 108 can be used for capturing thermal images or thermal video of at least a body part, for example anterior face, of the person. For example, a length of the captured thermal video may range from thirty seconds to one minute. According to an embodiment, during pre-processing the system 102 can receive a set of data packets associated with the captured one or more thermal images and/or the captured thermal video from the sensors 108 and process a set of frames in the captured thermal video and/or the captured one or more thermal images. The system 102 can detect and extract a predefined region, for example a face, of the subject in each frame of the captured images and/or videos, and segment one or more portions from the detected predefined region in each frame of the captured images and/or videos.

In another embodiment, the system 102 can identify a region of interest comprising arteries in the one or more segmented portions in each frame of the captured images and/or videos, and segment the identified region of interest from each of the captured any or a combination of the one or more images and videos. The system 102 can extract one or more pixel values, representing a set of biosignals, from each frame of the captured images and/or videos based on the segmented region of interest. The system 102 can further determine one or more parameters associated with a blood flow velocity and a blood pressure of the subject based on the extracted pixel values representing the set of biosignals, and compare the determined one or more parameters with predetermined set of reference parameters.

In an embodiment, the system can measure a risk score for the hypertension condition based on the comparison of the determined one or more parameters using computational models. The determined one or more parameters can be associated with potential biomarkers of arteriosclerosis and hemodynamic imbalances. A type and severity of the hypertension condition of the subject can be determined based on deviation of the determined one or more parameters with respect to the predetermined reference parameters and/or the measured risk score for the hypertension condition. The predetermined set of reference parameters can be stored in a database operatively coupled to the processing engine.

The determined one or more parameters associated with the blood flow velocity and the blood pressure can correspond to time and frequency domain parameters which can be any or a combination of average intensity, signal amplitude, signal period, signal entropy, signal power spectral density, histogram and peak count.

In an embodiment, evaluation of the hypertension condition of the subject may consider demographics and medical history of the subject along with the determined parameters for evaluating the hypertension conditions.

In an embodiment, the identified region of interest can be associated with a forehead region of the subject comprising frontal branches of the arteries which lay close to a skin surface on the forehead. The identified region of interest can be segmented based on a difference between thermal intensity along the arteries and a thermal intensity in other regions of the forehead. In an exemplary embodiment, the identified region of interest can be segmented using any or a combination of morphological operations, otsu thresholding, edge detection and contour approximations techniques.

In an embodiment, the system 102 can execute a first set of instructions associated with image filtering and enhancing techniques on each of the captured any or a combination of the images and videos for removing noise and improving quality.

In an embodiment, the predefined region such as the facial region in each frame of the captured images and/or videos can be detected based on execution of a second set of instruction associated with image processing including face detection and landmark detection techniques.

In an embodiment, the system 102 can perform spatial transformation on the identified region of interest to obtain a quantitative representation of a pattern observed in each frame of the captured any or a combination of the one or more images and videos, representing a set of biosignals waveform along an arterial section associated with pulsatile nature of blood flow.

In an embodiment, the system 102 can be configured to normalize and filter the one or more extracted pixel values representing the set of biosignals to determine time domain values by applying statistical analysis on the filtered pixel values.

In an exemplary embodiment, the system 102 can determine frequency domain values by applying Fast Fourier Transform and frequency filtering technique on the determined time domain values.

In an embodiment, the system 102 can determine, using signal processing techniques, signal parameters comprising the time and frequency domain parameters based on the determined frequency domain values and time domain values.

In an embodiment, the determined time and frequency domain parameters can be associated with any or a combination of the blood flow velocity and the blood pressure of the subject, general healthiness of the artery itself or physiological data indicating core temperature, blood density, arterial stiffness, and oxygen saturation in blood.

Figure 2:
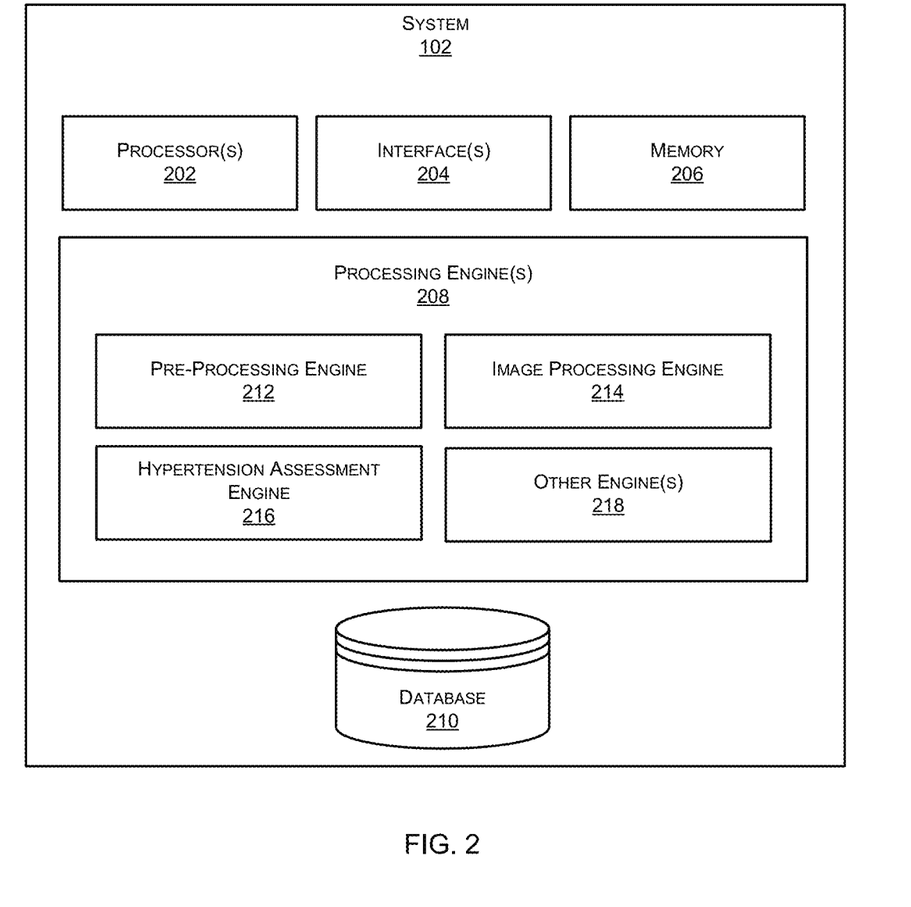
FIG. 2 illustrates exemplary functional components of the proposed system, in accordance with an embodiment of the present disclosure.

FIG. 2 illustrates exemplary functional components of the proposed system, in accordance with an embodiment of the present disclosure.

In an aspect, the system 102 may comprise one or more processor(s) 202. The one or more processor(s) 202 may be implemented as one or more microprocessors, microcomputers, microcontrollers, digital signal processors, central processing units, logic circuitries, and/or any device that manipulates data based on operational instructions. Among other capabilities, the one or more processor(s) 202 are configured to fetch and execute computer-readable instructions stored in a memory 206 of the system 102. The memory 206 may store one or more computer-readable instructions or routines, which may be fetched and executed to create or share the data units over a network service. The memory 206 may comprise any non-transitory storage device including, for example, volatile memory such as RAM, or non-volatile memory such as EPROM, flash memory, and the like.

The system 102 may also comprise an interface(s) 204. The interface(s) 204 may comprise a variety of interfaces, for example, interfaces for data input and output devices, referred to as I/O devices, storage devices, and the like. The interface(s) 204 may facilitate communication of system 102 with various devices coupled to the system 102. The interface(s) 204 may also provide a communication pathway for one or more components of the system 102. Examples of such components include, but are not limited to, processing engine(s) 208 and a database 210.

The processing engine(s) 208 may be implemented as a combination of hardware and programming (for example, programmable instructions) to implement one or more functionalities of the processing engine(s) 208. In examples described herein, such combinations of hardware and programming may be implemented in several different ways. For example, the programming for the processing engine(s) 208 may be processor-executable instructions stored on a non-transitory machine-readable storage medium and the hardware for the processing engine(s) 208 may comprise a processing resource (for example, one or more processors), to execute such instructions. In the present examples, the machine-readable storage medium may store instructions that, when executed by the processing resource, implement the processing engine(s) 208. In such examples, the system 102 may comprise the machine-readable storage medium storing the instructions and the processing resource to execute the instructions, or the machine-readable storage medium may be separate but accessible to system 102 and the processing resource. In other examples, the processing engine(s) 208 may be implemented by electronic circuitry.

The database 210 may comprise data that can be either stored or generated as a result of functionalities implemented by any of the components of the processing engine (s) 208. The database 210 may store a set of instructions, for example a first set of instructions, second set of instructions, and/or other required predetermined parameters data/instructions/algorithms to be used by the processors/processing engine 208.

In an exemplary embodiment, the processing engine(s) 208 may comprise a pre-processing engine 212, an image processing engine 214, a hypertension assessment engine 216 and other engines (s) 218.

It would be appreciated that modules being described are only exemplary modules, and any other module or submodule may be included as part of the system 102. These modules too may be merged or divided into super-modules or sub-modules as may be configured.

Pre-Processing Engine 212

Figure 4A:
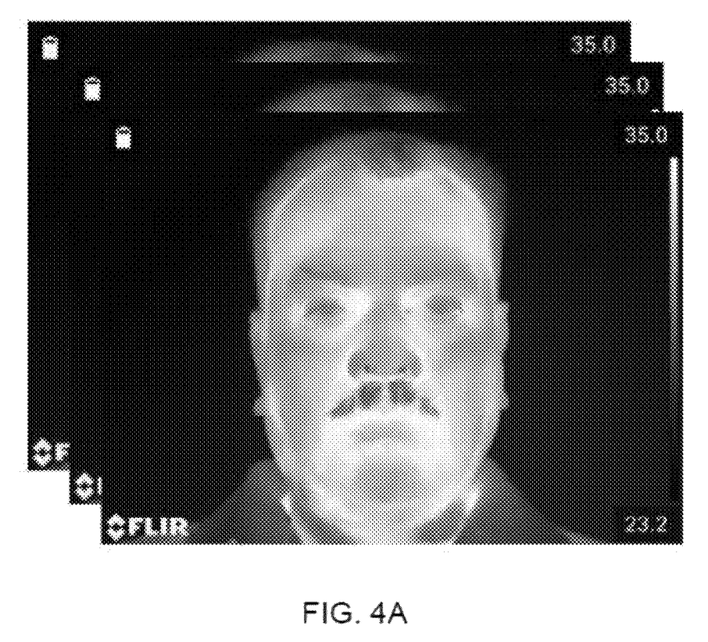
FIG. 4A illustrates a sequence of frames from captured thermal images/videos using an infrared thermal camera, in accordance with an embodiment of the present disclosure.
Figure 4B:
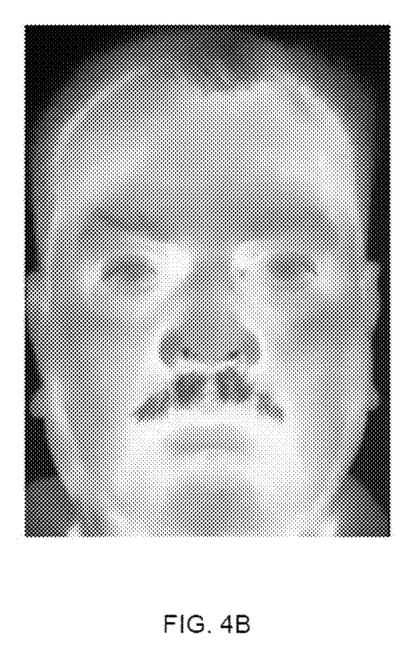
FIG. 4B illustrates a segment of a facial region detected using face detection technique and extracted from captured thermal images, in accordance with an embodiment of the present disclosure.

In an aspect, the pre-processing engine 212 receives a sequence of thermal image/video frames from the thermal sensors 108 of the computing device 106. FIG. 4A depicts a sequence of thermal image frames including anterior face obtained from the thermal sensors. The received thermal image/video frames may be converted into grayscale for processing. Further, the pre-processing engine 212 applies image filtering and enhancement techniques on the received frames to remove noise and ensure quality of the thermal images is sufficient before processing. The pre-processing engine 212 then uses a face detection model such as a haar cascade classifier on each of the frames in order to detect a predefined region such as a facial region, on the frame as shown in FIG. 4B. The pre-processing engine 212 can reject the captured thermal video/image when no face is detected. Further, the pre-processing engine 212 also uses tracking methods to detect and extract the facial region in subsequent frames to ensure a uniform set of frame segments.

In an embodiment, in order to ensure faster processing, the pre-processing engine 212 may perform contrast stretching, which is efficient as well as a computationally cheap technique implemented to enhance image quality. Those skilled in the art would appreciate that the pre-processing engine 212 focuses on enhancement and performs certain operations on the input image frames to ensure that processing in subsequent stages through the implementation of various other engines can be performed in less computational time. The enhancement of image frames can further be optimized to stay free from floating-point operations.

Image Processing Engine 214

Figure 4C:
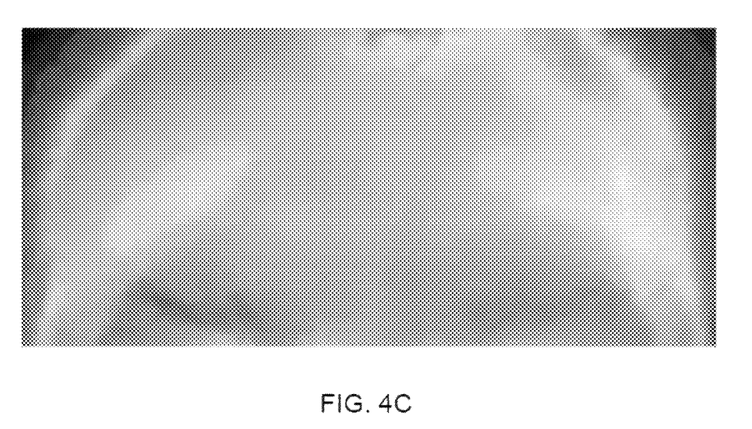
FIG. 4C illustrates a forehead region segmented from a face to identify a region of interest comprising arteries, in accordance with an embodiment of the present disclosure.

In an embodiment, the image processing engine 214 receives pre-processed frames of the thermal images/videos including the face region segmented in the frames. The image processing engine 214 may use facial landmark detection algorithms on the set of preprocessed frames to determine the position of the eyes or eyebrows in the facial region of the frames. The position of eyes obtained is further used to segment one or more portions such as a forehead region from the set of the preprocessed frames as shown in FIG. 4C. In another embodiment, the image processing engine 214 further defines a region of interest (ROI) for each image frame from a set of image frames received from the pre-processing engine 212. The defined region of interest includes various branches of the major arteries in the forehead, which is segmented based on heat distribution on the forehead. The image processing engine 214 may use a bilateral 2D filter on the segmented forehead region in each of the preprocessed frames to remove noise while preserving the edge due to the thermal intensity gradient. Further, since the region comprising the blood vessel is brighter than the surrounding region of the forehead due to heat emitted during blood flow, region of interest in each of the frames is segmented using a combination of morphological operations such as erosion and opening operation followed by Otsu thresholding, edge detection and contour approximations. The segments extracted from each of the set of frames resemble a vascular structure correlating to the arterial section.

Image segmentation is the process of partitioning a digital image into multiple regions or sets of pixels. Mostly, image partitions are different objects which have the same texture or color. The image segmentation results are a set of regions that cover the entire image together and a set of contours extracted from the image. All of the pixels in a region are similar with respect to some characteristics such as color, intensity, or texture. Adjacent regions are considerably different with respect to the same individuality. The different approaches include but are not limited to (i) by finding boundaries between regions based on discontinuities in intensity levels, (ii) thresholds based on the distribution of pixel properties, such as intensity values, and (iii) based on finding the regions directly. Thus, the choice of an image segmentation technique is depending on the problem being considered.

Region-based methods are based on continuity. These techniques divide the entire image into sub-regions depending on some rules like all the pixels in one region must have the same grey level. Region-based techniques rely on common patterns in intensity values within a cluster of neighboring pixels. The cluster is referred to as the region in addition to group the regions according to their anatomical or functional roles are the goal of the image segmentation. A threshold is the simplest way of segmentation. Using thresholding technique regions can be classified on the basis of range values, which is applied to the intensity values of the image pixels. Thresholding is the transformation of an input image to an output that is a segmented binary image segmentation methods based on finding the regions for abrupt changes in the intensity value.

When images are processed for enhancement, and while performing some operations like thresholding, more is the chance for distortion of the image due to noise. As a result, imperfections exist in the structure of the image. The primary goal of the morphological operation is to remove this imperfection that mainly affects the shape and texture of images. It is evident that morphological operations can be instrumental in image segmentation as the process directly deals with 'shape extraction' in an image. Morphology in the context of image processing means the description of the shape and structure of the object in an image. Morphological operations work on the basis of set theory and rely more on the relative ordering of the pixel instead of the numerical value. This characteristic makes them more useful for image processing. Those skilled in the art would appreciate the significance of these techniques in the image segmentation.

Figure 4D:
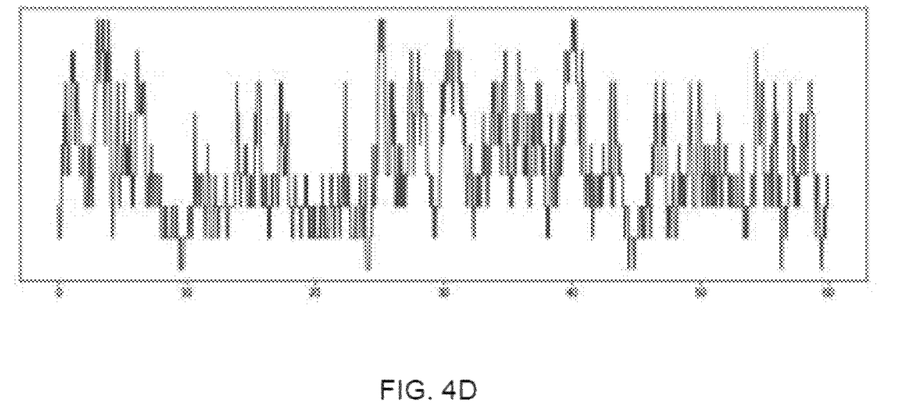
FIG. 4D illustrates an exemplary biosignal waveform determined from pixel values extracted from a region of interest, in accordance with an embodiment of the present disclosure.

In an embodiment, the image processing engine 214 uses the segmented regions to extract pixel values from each of the frames for describing the changes in the temperature over time. The change in these pixel values correlates with transmission of the blood through the arterial cross-section. The pixel values in the region of interest are spatially transformed to obtain a quantitative representation for the pattern observed in each frame. The spatial transformation includes applying block-based averaging functions and determining the maximum pixel intensity values along the cross-sectional axis. The values can be represented as a series $$X(t)_1^T = \text{Max}_{i=0,j=0}^{i+B_w<=w, j+B_h<=h} \left[ \left( \sum_{x=i}^{B_w} \sum_{y=j}^{B_h} P(x,y) \right) / (B_w * B_h) \right]$$

where X(t) is the time domain value for the frame t, P(x,y) is the pixel intensity at position (x,y), $B_w$, $B_h$ is the width and height of the block. The extracted values are represented as a set of one or more time domain biosignals which are then used by other modules/engines to evaluate and measure parameters correlating the inconsistencies in the systolic and diastolic blood pressure. FIG. 4D illustrates an exemplary biosignal waveform extracted from the region of interest of an individual.

Hypertension Assessment Engine 216

In an embodiment, the hypertension assessment engine 216 is used for identifying between primary and secondary forms and for determining severity of the hypertension condition or risk of developing hypertension by calculating and comparing parameters pertaining a blood flow velocity and a blood pressure. The pixel values representing the set of biosignals extracted from the image processing engine 214 are initially normalized using min-max normalization. The normalized time data is then transformed to obtain frequency domain data using the function, P(X)

$$\omega(k)_0^T = F_{f=0.67}^{1.67} \left[ \sum_{n=0}^{N} X[n] e^{(-2\pi i k n)/N} \right]$$

where the assessment engine 216 uses Fast Fourier Transform on the data to obtain frequency domain values. The frequency values are then filtered 'F' to select the frequencies in between 0.67 Hz and 1.7 Hz in order to select the signal in the frequency range of the pulse. The assessment engine 216 further applies signal processing techniques on these filtered data to calculate time and frequency domain parameters such as, but not limited to, average intensity, signal amplitude, signal period, signal entropy, signal power spectral density, histogram and peak count for each of the signals obtained independently. The combination of one or more of these parameters is associated with the determined parameters associated with the blood flow velocity and blood pressure. This assessment is subject to thermal pattern analysis and signals analysis on the pulsatile nature of thermal changes in accordance with the pulsatile blood flow.

Figure 5A:
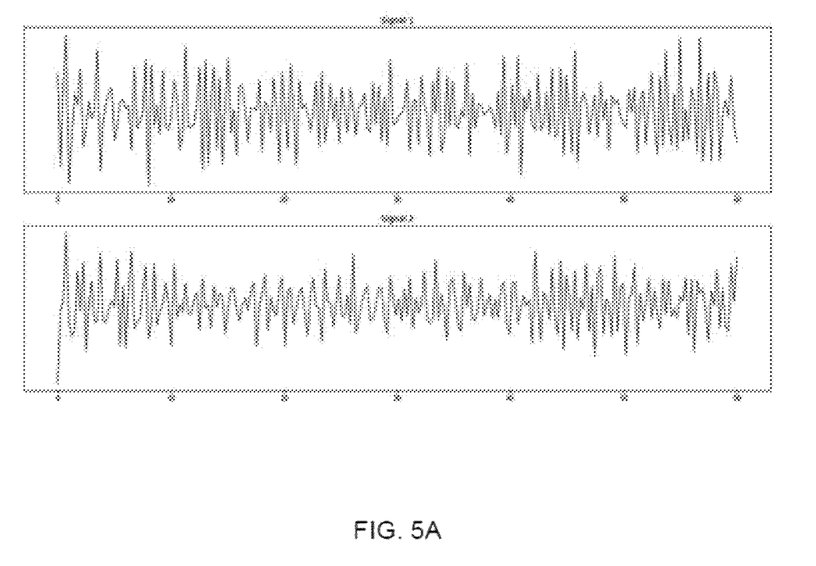
FIG. 5A illustrates two exemplary biosignals obtained and filtered from a region of interest of a healthy person, in accordance with an embodiment of the present disclosure.
Figure 5B:
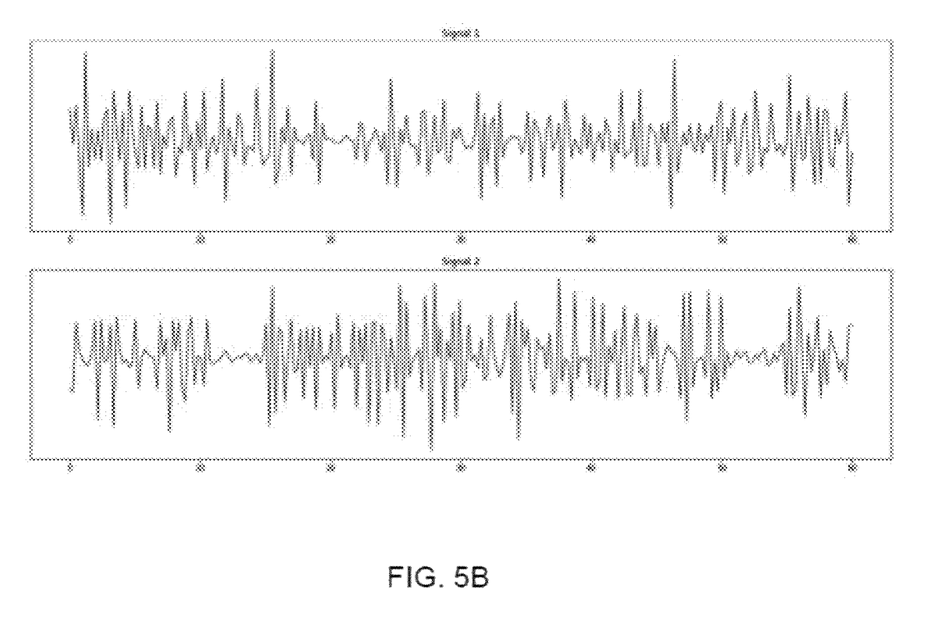
FIG. 5B illustrates two exemplary biosignals obtained and filtered from a region of interest of a chronic hypertensive person, in accordance with an embodiment of the present disclosure.

In another embodiment, the computation models in the hypertension assessment engine 216 can be initially developed by first calculating the signal parameters for the set of signals extracted from the region of interest of both the healthy an individual and primary and secondary hypertensive patients. The assessment engine 216 applies principal component analysis on the calculated signal parameters of the healthy individual and the hypertensive patient to determine parameters that are most relevant in determining the hypertension conditions. The set of selected parameters are further analyzed and compared using statistical methods to identify variations and relative differences between the signals extracted from healthy individual and hypertensive patient. FIGS. 5A and FIG. 5B illustrates the set of two filtered signals obtained from a healthy individual and a chronic hypertensive patient respectively. As shown, the two signals from the healthy individual in the FIG. 5A are similar while the signals from the hypertenisve person are different and show temporal variations. The variations and the differences are further analyzed to differentiate between the primary and secondary form of hypertensions. The variations define the imbalances associated with vascular dysfunction and hemodynamic changes in the arteries and can be normalized based on age and other physical factors. The set of parameters and the variations identified are then structured as the training data to train the computation models using machine learning units including algorithms for classifying and scoring the hypertension conditions of a person. The score obtained using the computation model can be formulated as:

$$S=z/(1+z)$$

where, $z=e^{\sum_{i=1}^{n}(w_i p_i)}$ where $w_i p_i$ represents the weighted sum of the set of selected signal parameters.

In an embodiment, the assessment engine 216 uses the computational models on the determined parameters to determine a risk score that relates to severity of the hypertension condition. The risk score can have a value on a scale like 0-1, 1-10, where the severity increases with the increase in score value. The assessment can also take into consideration demographics and medical history for comparing and calculating the hypertension risk score. The hypertension risk score can be used either to measure the hypertension condition or to evaluate the risk of developing the primary hypertensions or secondary hypertension.

Figure 3:
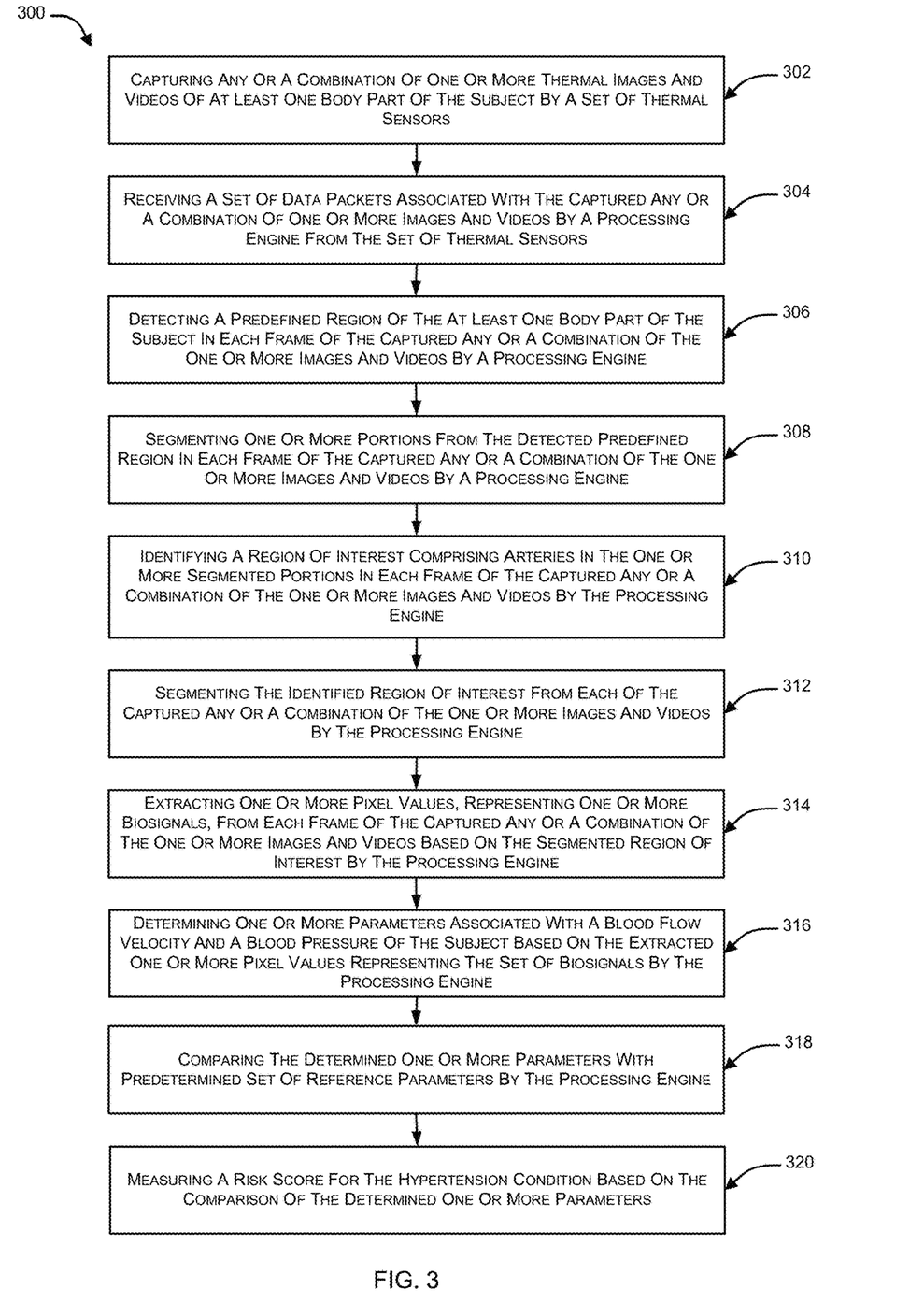
FIG. 3 illustrates a flow diagram illustrating a method for measuring hypertension condition of a subject, in accordance with an embodiment of the present disclosure.

FIG. 3 illustrates a flow diagram of the proposed method for measuring the hypertension health condition of a person, in accordance with an embodiment of the present disclosure.

In an aspect, the proposed method may be described in the general context of computer-executable instructions. Generally, computer-executable instructions include routines, programs, objects, components, data structures, procedures, modules, functions, etc. that perform particular functions or implement particular abstract data types. The method can also be practiced in a distributed computing environment where functions are performed by remote processing devices that are linked through a communications network. In a distributed computing environment, computer-executable instructions may be located in both local and remote computer storage media, including memory storage devices.

The order in which the method as described is not intended to be construed as a limitation and any number of the described method blocks may be combined in any order to implement the method or alternate methods. Additionally, individual blocks may be deleted from the method without departing from the spirit and scope of the subject matter described herein. Furthermore, the method may be implemented in any suitable hardware, software, firmware, or combination thereof. However, for ease of explanation, in the embodiments described below, the method may be considered to be implemented in the above-described system.

In the context of a flow diagram 300, a block 302 pertains to capturing any or a combination of one or more thermal images and videos of at least one body part, for example an anterior face, of the subject by a set of thermal sensors.

Further, a block 304 pertains to receiving a set of data packets associated with the captured any or a combination of one or more images and videos by a processing engine from the set of thermal sensors. The processing engine may perform pre-processing on the thermal images or thermal videos received from the set of thermal sensors for noise reduction and quality enhancement.

Further, a block 306 pertains to detecting a predefined region, for example a facial region, of the subject in each frame of the captured any or a combination of the one or more images and videos by the processing engine on receipt of the set of data packets.

Further, a block 308 pertains to segmenting one or more portions, for example a forehead, from the detected predefined region in each frame of the captured any or a combination of the one or more images and videos by the processing engine, and a block 310 pertains to identifying a region of interest comprising one or more arteries in the one or more segmented segmented/forehead portions in each frame of the captured any or a combination of the one or more images and videos by the processing engine.

Further, a block 312 pertains to segmenting the identified region of interest from each of the captured any or a combination of the one or more images and videos by the processing engine, and a block 314 pertains to extracting one or more pixel values, representing one or more biosignals, from each frame of the captured any or a combination of the one or more images and videos based on the segmented region of interest by the processing engine, Further, a block 316 pertains to determining one or more parameters associated with a blood flow velocity and a blood pressure of the subject based on the extracted one or more pixel values representing the set of biosignals by the processing engine, and a block 318 pertains to comparing the determined one or more parameters with predetermined set of reference parameters by the processing engine.

Further, a block 320 pertains to measuring a risk score for the hypertension condition based on the comparison of the determined one or more parameters. The risk score can be measured using computational models. The determined one or more parameters are associated with arteriosclerosis and hemodynamic factors and can correspond to time and frequency domain parameters such as average intensity, signal amplitude, signal period, signal entropy, signal power spectral density, histogram and peak count.

In an embodiment, the measured risk score relates to abnormal blood pressure levels and vascular impairment caused by hypertension.

In an embodiment, a process of generating the computational models can include (a) calculating signal parameters for one or more signals associated with the arterial section of both healthy subjects and hypertensive patients; (b) identifying a set of parameters that correlate to complications associated with a primary hypertension condition and a secondary hypertension condition using a principal component analysis on the calculated signal parameters; (c) determining patterns and differences among the parameters between the hypertensive and healthy subjects by using statistical methods and visualization; and (d) training the computing models by using machine learning units/algorithms comprising clustering models, logistic regression, random forest, neural network model on the set of parameters.

Thus, the present disclosure provides a non-invasive, non-contact passive system method for risk assessment and measurement of primary and secondary hypertension conditions of an individual includes assessing biomarkers pertaining to arteriosclerosis and hemodynamic imbalances of the individual from the thermal image/video. The passive thermal images/videos comprising a front face of a person are acquired using a thermal infrared camera to auto-detect and segment frontal branches of major arterial regions from a forehead region. The frontal branches of the arteries are segmented based on heat variations on the forehead. Tracking methods are used to segment an identified region of interest from the forehead in a sequence of thermograms. Parameters indicating cardiovascular health are calculated from the segmented region of interest by applying thermal pattern analysis and signal analysis on pulsatile nature of thermal changes in accordance with the pulsatile blood flow. The system and method includes analysis of determined parameters to identify imbalances and deviations of values from predetermined normal/reference range. The state of hypertension condition is measured based on imbalances in the determined parameters that correlate to inconsistencies in the systolic and diastolic blood pressure.

Thus, it will be appreciated by those of ordinary skill in the art that the diagrams, schematics, illustrations, and the like represent conceptual views or processes illustrating systems and methods embodying this invention. The functions of the various elements shown in the figures may be provided through the use of dedicated hardware as well as hardware capable of executing associated software. Similarly, any switches shown in the figures are conceptual only. Their function may be carried out through the operation of program logic, through dedicated logic, through the interaction of program control and dedicated logic, or even manually, the particular technique being selectable by the entity implementing this invention. Those of ordinary skill in the art further understand that the exemplary hardware, software, processes, methods, and/or operating systems described herein are for illustrative purposes and, thus, are not intended to be limited to any particular name.

While embodiments of the present invention have been illustrated and described, it is apparent that the invention is not limited to these embodiments only. Numerous modifications, changes, variations, substitutions, and equivalents will be apparent to those skilled in the art, without departing from the spirit and scope of the invention, as described in the claim.

In the foregoing description, numerous details are set forth. It is apparent, however, to one of ordinary skill in the art having the benefit of this disclosure, that the present invention may be practiced without these specific details. In some instances, well-known structures and devices are shown in block diagram form, rather than in detail, to avoid obscuring the present invention.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously. Within the context of this document terms "coupled to" and "coupled with" are also used euphemistically to mean "communicatively coupled with" over a network, where two or more devices are able to exchange data with each other over the network, possibly via one or more intermediary devices.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refer to at least one of something selected from the group consisting of A, B, C . . . and N, the text should be interpreted as requiring only one element from the group, not A plus N, or B plus N, etc.

While the foregoing describes various embodiments of the invention, other and further embodiments of the invention may be devised without departing from the basic scope thereof. The scope of the invention is determined by the claims that follow. The invention is not limited to the described embodiments, versions or examples, which are included to enable a person having ordinary skill in the art to make and use the invention when combined with information and knowledge available to the person having ordinary skill in the art.

Advantages of the Present Disclosure

The present disclosure provides a simple and efficient solution which can obviate the foregoing limitations in the art.

The present disclosure provides an improved system for evaluating hypertension conditions of an individual.

The present disclosure provides an efficient system to identify individuals with either pre-hypertensive or hypertensive conditions and to determine between primary and secondary forms so that they can obtain treatment early, and can also monitor progression of the disease over time.

The present disclosure provides a non-contact, non-invasive system and method for evaluating a primary hypertension condition and/or a secondary hypertension condition of a person by measuring vascular health using thermal imaging.

The present disclosure provides an efficient system and method to use biomarkers associated with vascular health and various hemodynamic factors determined from thermal imaging for evaluating hypertension conditions of individuals to help in diagnosis of health conditions.

The present disclosure provides a simple and cost-effective system and method which can be easily implemented for measuring hypertension conditions of a person.

We claim:

1. A system for measuring a hypertension condition of a subject, the system comprising:
   a set of thermal sensors for capturing one or more of thermal images and/or one or more of thermal videos of at least one body part of the subject; and
   a processing engine operatively coupled to the set of thermal sensors, and comprising one or more processors coupled to a memory, the memory storing a set of instructions executable by the one or more processors to:
   receive a set of data packets associated with the captured one or more of thermal images and/or one or more of thermal videos from the set of thermal sensors;
   detect a predefined region of the at least one body part of the subject in each frame of the captured one or more of thermal images and/or one or more of thermal videos on receipt of the set of data packets;

segment one or more portions from the detected predefined region in each frame of the captured one or more of thermal images and/or one or more of thermal videos;

identify a region of interest comprising one or more arteries in the segmented one or more portions in each frame of the captured one or more of thermal images and/or one or more of thermal videos;

segment the identified region of interest from each frame of the captured one or more thermal images and/or one or more of thermal videos;

extract one or more pixel values, representing a set of biosignals, from each frame of the captured one or more of thermal images and/or one or more of thermal videos based on the segmented region of interest;

determine one or more parameters associated with a blood flow velocity and a blood pressure of the subject based on the extracted one or more pixel values representing the set of biosignals;

compare the determined one or more parameters with a predetermined set of reference parameters; and measure a risk score for the hypertension condition based on the comparison of the determined one or more parameters, wherein the determined one or more parameters are associated with a blood density and a pulse rate of the subject, and wherein a primary hypertension condition and a secondary hypertension condition are determined based on the measured risk score for the hypertension condition; and wherein the measurement of the risk score for the hypertension condition is performed using computational models, and wherein generation of the computational models comprises:

calculating signal parameters for one or more signals associated with a corresponding arterial section of a healthy subject and a corresponding arterial section of a hypertensive subject;

identifying a set of parameters that correlate to complications associated with the primary hypertension condition and the secondary hypertension condition using a principal component analysis on the calculated signal parameters;

determining patterns and differences among the signal parameters between the hypertensive subject and the healthy subject by using statistical methods and visualization; and training the computational models by using machine learning units comprising clustering models, a logistic regression, random forest, and a neural network model on the set of parameters.

2. The system as claimed in claim 1, wherein the set of thermal sensors are associated with one or more of a digital camera, a digital single-lens reflex (DSLR) camera, and an infrared thermal camera, and wherein the set of thermal sensors sense heat or infrared radiation emitted from the at least one body part of the subject and renders the one or more of thermal images and/or one or more of thermal videos representing a spatial intensity of radiation.

3. The system as claimed in claim 1, wherein the determined one or more parameters are associated with potential biomarkers of arteriosclerosis and hemodynamic imbalances, and wherein the predetermined set of reference parameters are stored in a database operatively coupled to the processing engine.

4. The system as claimed in claim 1, wherein the subject is a human.

5. The system as claimed in claim 1, wherein the at least one body part of the subject is an anterior face of the subject, and wherein the segmented one or more portions are associated with a forehead of the subject.

6. The system as claimed in claim 5, wherein the identified region of interest is associated with a forehead region of the subject comprising frontal branches of the arteries on the forehead.

7. The system as claimed in claim 6, wherein the identified region of interest is segmented based on a difference between thermal intensity along the arteries and a thermal intensity in other regions of the forehead.

8. The system as claimed in claim 7, wherein the identified region of interest is segmented using any or a combination of morphological operations, otsu thresholding, edge detection and contour approximations techniques as the region of interest comprising one or more arteries that are brighter than a surrounding region of the forehead area.

9. The system as claimed in claim 1, wherein the one or more processors are configured to execute a first set of instructions associated with image filtering and enhancing techniques on each of the captured one or more of thermal images and/or one or more of thermal videos for removing noise and improving quality.

10. The system as claimed in claim 1, wherein the one or more processors are configured to execute a second set of instructions associated with image processing including face detection and landmark detection techniques to detect the predefined region of the at least one body part in each frame of the captured one or more of thermal images and/or one or more of thermal videos.

11. The system as claimed in claim 1, wherein the one or more processors are configured to perform spatial transformation on the identified region of interest to obtain a quantitative representation of a pattern observed in each frame of the captured one or more of thermal images and/or one or more of thermal videos, representing a set of biosignal waveforms along an arterial section associated with pulsatile nature of blood flow.

12. The system as claimed in claim 1, wherein the one or more processors are configured to normalize and filter the one or more extracted pixel values representing the set of biosignals, and wherein the one or more processors are configured to determine time domain values by applying the statistical methods on the one or more extracted pixel values.

13. The system as claimed in claim 12, wherein the one or more processors are configured to determine frequency domain values by applying Fast Fourier Transform and frequency filtering technique on the determined time domain values.

14. The system as claimed in claim 13, wherein the one or more processors are configured to determine, using signal processing techniques, signal parameters comprising time and frequency domain parameters based on the determined frequency domain values and time domain values.

15. The system as claimed in claim 14, wherein the determined time and frequency domain parameters comprises any or a combination of average intensity, signal amplitude, signal period, signal entropy, signal power spectral density, histogram and peak count, and wherein the time and frequency domain parameters are also associated with any or a combination of the blood flow velocity and the blood pressure of the subject, general healthiness of the one or more arteries or physiological data indicating core temperature, the blood density, arterial stiffness, and oxygen saturation in blood.

16. The system as claimed in claim 1, wherein the measurement of the risk score for the hypertension condition of the subject considers demographics and a medical history of the subject along with the determined one or more parameters for evaluating the hypertension condition.

17. A method for measuring a hypertension condition of a subject, the method comprising:
    capturing, by a set of thermal sensors, one or more of thermal images and/or one or more of thermal videos of at least one body part of the subject;
    receiving, by a processing engine, a set of data packets associated with the captured one or more of thermal images and/or one or more of thermal videos from the set of thermal sensors operatively coupled to the processing engine;
    detecting, by the processing engine, a predefined region of the at least one body part of the subject in each frame of the captured one or more of thermal images and/or one or more of thermal videos on receipt of the set of data packets;
    segmenting, by the processing engine, one or more portions from the detected predefined region in each frame of the captured one or more of thermal images and/or one or more of thermal videos;
    identifying, by the processing engine, a region of interest comprising arteries in the one or more segmented portions in each frame of the captured one or more of thermal images and/or one or more of thermal videos;
    segmenting, by the processing engine, the identified region of interest from each of the captured one or more of thermal images and/or one or more of thermal videos;
    extracting, by the processing engine, one or more pixel values, representing a set of biosignals, from each frame of the captured one or more of thermal images and/or one or more of thermal videos based on the segmented region of interest;
    determining, by the processing engine, one or more parameters associated with a blood flow velocity and a blood pressure of the subject based on the extracted one or more pixel values representing the set of biosignals;
    comparing, by the processing engine, the determined one or more parameters with a predetermined set of reference parameters; and
    measuring, by the processing engine, a risk score for the hypertension condition based on the comparison of the determined one or more parameters,
    wherein the determined one or more parameters are associated with a blood density and a pulse rate of the subject, and wherein a primary hypertension condition and a secondary hypertension condition are determined based on the measured risk score for the hypertension condition; and
    wherein the measurement of the risk score for the hypertension condition is performed using computational models, and wherein generation of the computational models comprises:
        calculating signal parameters for one or more signals associated with a corresponding arterial section of a healthy subject and a corresponding arterial section of a hypertensive subject;
        identifying a set of parameters that correlate to complications associated with the primary hypertension condition and the secondary hypertension condition using a principal component analysis on the calculated signal parameters;
        determining patterns and differences among the signal parameters between the hypertensive subject and the healthy subject by using statistical methods and visualization; and
        training the computational models by using machine learning units comprising clustering models, a logistic regression, random forest, and a neural network model on the set of parameters.

* * * * *